United States Patent [19]

Cox et al.

[11] Patent Number: 4,745,215

[45] Date of Patent: May 17, 1988

[54] FLUORINE CONTAINING DICYANATE RESINS

[75] Inventors: Robert J. Cox, Watsonville, Calif.; William J. Summa, Endwell; David W. Wang, Vestal, both of N.Y.

[73] Assignee: International Business Machines Corporation, Armonk, N.Y.

[21] Appl. No.: 33,557

[22] Filed: Apr. 3, 1987

[51] Int. Cl.$^4$ .................... C07C 71/00; C08G 73/00; B32B 27/00
[52] U.S. Cl. .................... 560/301; 528/422; 525/424; 428/422.8
[58] Field of Search .................... 560/301, 359

[56] References Cited

U.S. PATENT DOCUMENTS

| | | | |
|---|---|---|---|
| 3,180,883 | 4/1965 | Case | 560/359 |
| 3,294,713 | 12/1966 | Hudson et al. | 560/359 |
| 3,681,292 | 8/1972 | Loudas | 560/301 |
| 3,707,486 | 12/1972 | Oertel | 560/359 |
| 3,829,460 | 8/1974 | Buttner | 560/359 |
| 4,477,629 | 10/1984 | Hefner | 560/301 |

*Primary Examiner*—Alan Siegel
*Attorney, Agent, or Firm*—Perman & Green

[57] ABSTRACT

4,4'-(Hexafluoroisopropylidene) bisphonol dicyanate and related compounds have reduced dielectric constant, reduced moisture absorption, and increase Tg making such compounds especially suitable for various electronic applications, such as circuit packaging or in forming prepregs and circuit boards.

5 Claims, No Drawings

FLUORINE CONTAINING DICYANATE RESINS

BACKGROUND OF THE INVENTION

I. Field of the Invention

This invention relates to fluorine-containing dicyanates, cyanurate polymers produced therefrom, as well as blends of the dicyanates with both thermosetting and thermoplastic polymers. In a further aspect it relates to shaped articles, such as reinforced resin laminates used in electronic applications, made from the cyanurate polymers.

II. Description of the Prior Art

It is known to react polyphenols with cyanogen halides to give aromatic cyanic acid esters (German Published Specification No. 1,195,764). It is also known that 2,2-bis-(4-hydroxyphenol) propane may be reacted with cyanogen chloride to form the corresponding dicyanate compound (U.S. Pat. No. 4,060,541). It is also known that methylol-terminated fluorocarbons may be reacted with cyanogen halides to produce fluorocarbon cyanates which can be polymerized to produce polyfluorocyanurates U.S. Pat. No. 3,681,292). It is also known to blend cyanate-containing polymers with epoxy resins (U.S. Pat. No. 4,477,629).

SUMMARY OF THE INVENTION

It has now been found, surprisingly, that the cyanate resins which contain a $CF_3$—C—$CF_3$ group between aromatic rings have unexpectedly low dielectric constants, very low moisture absorption, good thermal stability and a high glass transition temperature (Tg). In addition these resins readily form alloys with both thermoplastic and thermosetting resins thereby allowing them to be used for a variety of electronic applications, i.e. packaging or circuit boards.

DETAILED DESCRIPTION OF THE INVENTION

The fluorine containing dicyanate compounds of the present invention have the formula

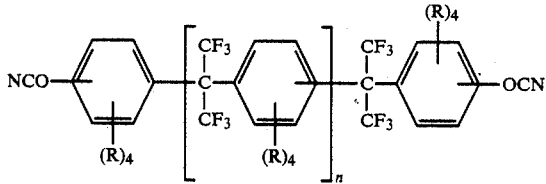

wherein the R groups are each independently selected from hydrogen, alkyl with 1 to about 8 carbon atoms, alkenyl with 2 to about 8 carbon atoms, aryl or alkaryl with 6 to about 12 carbon atoms, and halogen, and n is an integer from 0 to about 4. Preferably all of the R's are hydrogen and n is either 0 or 1. Most preferably the compound has the formula

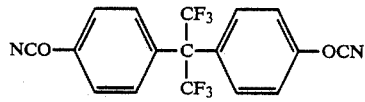

The dicyanates of the above formulae may be prepared by reacting the corresponding dihydroxy, i.e. diphenol, compound with a cyanogen halide in the presence of a base. Generally the amount of cyanogen halide is in excess of stoichiometric. Because of the exothermic nature of the reaction and the desire to prevent it from running away with consequent loss of reactants, and because of the volatility of the cyanogen halide, low temperatures below the boiling points of the reactants are maintained. Generally, low temperatures in the range of −40° to 40° C., preferably −20° to 0° C., will be used in the reaction carried out in an inert liquid organic solvent. Solvents useful for this purpose representatively include acetone, ether, tetrahydrofuran, aromatic hydrocarbons such as benzene, toluene, and xylene, and halogenated aliphatic or aromatic hydrocarbons.

Cyanogen halides which can be used include cyanogen chloride (the preferred cyanating agent) and cyanogen bromide, these cyanating agents being well-known compounds which are commercially available or which can be prepared by well-known methods. Stoichiometrically, one mole of cyanogen halide is reacted with one equivalent of a hydroxyl group in the reactant; however, we prefer to use an amount in excess of stoichiometric, e.g. cyanogen halide up to 50% excess.

The base, which may be either organic or inorganic, is utilized in an amount sufficient to neutralize the hydrogen halide produced in the reaction. Suitable such bases include amines, oxides, hydroxides, carbonates, and bicarbonates. Preferably, the base is a tertiary amine like triethylamine or an alkali metal hydroxide like sodium hydroxide.

In general, the process is carried out by suspending and/or dissolving the dihydroxy compound and the cyanogen halide in an inert solvent and then adding the base. After cyanation is completed, the dicyanate product may be recovered from the reaction mixture by any suitable recovery process, such as precipitation, extraction, distillation, crystallization, or the like. Preferably, the product is recovered by pouring the reaction mixture into water thereby causing the dicyanate to precipitate out.

It has been found that the above-described dicyanates are particularly useful as monomers, intermediates or prepolymers for the preparation of cyanurate polymers. Polymerization of the dicyanates is accomplished by heating the cyanates to effect their thermal polytrimerization. Homopolymers of the dicyanates as well as copolymers with other dicyanates can be prepared in this fashion. The polymers will have a three-dimensional network structure with fluorine-containing groups linking the various cyanurate rings.

Generally, the polymerization of cyanates, in accordance with this invention, will be carried out by first melting the cyanate monomeric material to obtain a homogenous melt and then raising the temperature in a range of about 50° to 350° C., preferably about 75° to 300° C. Alternatively, this polymerization can be carried out with the aid of activators, initiators, or catalysts. These polymerization promoting agents representatively include Lewis acids, such as aluminum chloride, boron trifluoride, ferric chloride, titanium chloride, and zinc chloride; protonic acids, such as hydrochloric and the other mineral acids; salts of weak acids, such as sodium acetate, sodium cyanide, sodium cyanate, potassium thiocyanate, sodium bicarbonate, and sodium boronate, and bases, such as sodium methoxide, sodium hydroxide, pyridine, triethylamine, and the like. Preferred catalysts are metal carboxylates and metal chelates, such as cobalt, iron, zinc, and copper acetyl acetonates or octoates or naphthenates. The amount of catalyst used can vary, and generally will be 0.5 to 5 mole percent, preferably 0.05 to 0.1 mole percent.

The polymerization of the cyanates can also be carried out by polymerizing them in solution or in suspension, using as a solvent or suspension medium the common organic solvents such as hydrocarbons, ketones, halogenated hydrocarbons, nitrated hydrocarbons, dimethylsulfoxide, dimethylformamide or ether. The solvent can be removed by distillation or simple evaporation during the course of, or at the end of the polymerization.

The cyanuarate polymers of this invention possess stability at elevated temperatures along with resistance to solvents and corrosive chemicals. They can be used as one-component cured-in-place systems. Shaped articles having plastic properties can be readily fabricated from these polymers. Also, the polymers can be applied to reinforcement materials to produce prepregs for subsequent lamination into circuit boards. The fabrication of shaped articles is greatly facilitated by the fact that no volatile by-products are evolved during the curing process. The plastics are tough and strong with high glass transition and heat distortion temperatures.

In addition, the dicyanate or a prepolymer thereof can be blended with either thermosetting or thermoplastic resins to form novel resin systems which can benefit from the properties of each component. Suitable thermosetting resins useful herein include: epoxies, acrylates, bismaleimides, polyarylacetylenes, vinyl or acetylene terminated benzene, thiophenols, phenols, polyimides, polyisoimides, polysulfones, polycarbonates, polyetherketones, poly(phenyl-astriazine)s, polyphenylenes, polyphenylquinoxalines, polyquinolines, polybenzimidazoles, polybenzothiazoles and the like. Suitable thermoplastic resins useful for blending include polyetherimides, polyimides, polyarylates, siloxane polyimides, fluorine containing polyimides, polyarcylates, polysulfones, polycarbonates, polyphenylquinoxalines, polybenzoimidazoles, rubbers, and the like.

Furthermore, with the incorporation of proper photoinitiators, the resin compositions can also be used in lithographic-photoresist type applications.

The resins of the present invention can be used wherever there is need for a material which requires a low dielectric constant, i.e. less that 3 and preferably less than 2.8, low moisture absorption, good thermostability, some flame resistance, and a high Tg. One particular such use is in the manufacture of prepregs, reinforced composites, which go into the formation of printed circuit boards. The cyanate resins are used to make prepregs by being combined with fabrics of chopped fibers of such as glass, polyaramid, quartz, polytetrafluroethylene, poly(phenylenebenzbisthiazole), and the like.

Having described the basic concepts of the present invention, reference is now made to the following examples, which are provided by way of illustration, and not by way of limitation, of the practice of the present invention. All parts and percents are by weight unless otherwise specified.

EXAMPLE I 4,4'-Hexafluoroispropylidenediphenol (6.74 g.) and cyanogen bromide (4.24 g.) were dissolved in 50 ml. of acetone. To this solution was added 5.6 ml of triethylamine dropwise with stirring while maintaining the temperature at about 0° C. via a ice-bath. The reaction continued for about 30 minutes. Triethyleneamine hydrobromide precipitated out of solution and the reaction mixture was poured into water. The desired dicyanate precipitated out of the aqueous solution and was filtered, water washed and dried. The slightly yellow solid was examined by IR and found to have no OH bands and a new resonance at 2270 cm$^{-1}$ confirming the replacement of the phenolic groups by cyanate groups. A yield of 7 g. of pure dicyanate was obtained.

EXAMPLE II

The procedure of Example I is repeated except that the diphenol compound is replaced by 11.24 g of the following polyfluorobisphenol:

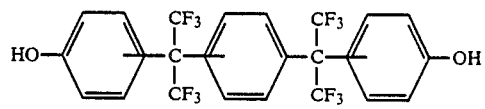

The formation of the desired dicyanate may be confirmed by infrared analysis.

EXAMPLE III

The polytrimerization of the compound of Example I was performed as follows: 0.25 g. of 4,4'-(hexafluoroisopropylidene) bisphenol dicyanate and 0.005 g. of zinc octoate were mixed with 0.5 g. of methylethylketone at room temperature. After filtration, the resultant varnish was placed on a glass slide and dried under vacuum. A portion of the dried polymer powder (10.20 mg) was placed in an aluminum pan and cured in a Perkin Elmer DSC-4 differential scanning calorimeter at 300° C. for 30 minutes. The DSC thermogram result was a Tg of 243° C.

EXAMPLE IV

In order to compare the properties of one of the fluorinated dicyanates of the present invention with those of its closest non-fluorinated homologue, the procedure of Example I was repeated to produce (i) the hexafluoro compound of Example I (6F-DI-CY) and (ii) the non-fluorine containing bisphenol A dicyanate (DI-CY) which has the formula

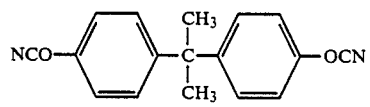

These compounds and their polymers were evaluated and found to have the properties shown in Table I.

TABLE I

|  | DICY | CF-DI-CY |
|---|---|---|
| MONOMER | | |
| Melting Point (°C.) | 79.3 | 87 |
| CURED RESIN | | |
| Specific Gravity | 1.20 | 1.46 |
| Dielectric Constant (at 1100 MHz) | 2.97 | 2.70 |
| Tg (°C.)* | | |
| Cured at 240° C. | 240 | 240–260 |
| Post cured at 330° (N$_2$) | 290 | 300–310 |
| Post cured at 330° (Air) | 235 | |
| Coefficient of Thermal Expansion (ppm/°C.) | 41 | 50 |

TABLE I-continued

|  | DICY | CF-DI-CY |
|---|---|---|
| TGA Decomposition Onset (N$_2$) (°C.) | 452 | 452 |
| Moisture Absorption %** | | |
| 24 hours at room temp. | 0.68 | 0.46 |
| 33 days at room temp. | 1.37 | 0.86 |
| 16 hours boiling water | 1.74 | 1.31 |

*Onset glass transition temperature as measured by differential scanning calorimeter (DSC)
**Performed after curing at 240° C. for 1.5 hours.

As can be seen the compound of the present invention was found to have a substantially reduced dielectric constant and moisture absorption while also having an increased Tg as compared to its closest non-fluorinated homologue.

EXAMPLE V

To determine the ability of the compounds of the present invention to be blended with thermosetting and thermoplastic resins, the following was performed:

A solvent mixture of 2 parts N-methylpyrollidone and 1 part p-xylene was prepared. To portions of the mixture were added the polymers shown in Table II together with the compound of Example I (GF-DI-CY) to form solutions containing 25% solids. The solutions were then cast onto a piece of aluminum foil and cured at a temperature of 360°–436° C. for 2.3 hours. The resultant alloys were examined for phase separation with the results also shown in Table II. XU-218 polyimide is a product of Ciba-Geigy prepared from 5(6)-amino-1-(4'-aminophenyl)-1,2,2-trimethylindane and benzophenone tetracarboxylic anhydride. Thermid IP-600 polyimide is an acetylene terminated polyisoimide oligomer marketed by National Starch and Chemical Company.

The results clearly show that the compounds of the present invention may be blended with both thermoplastic and thermosetting resins.

TABLE II

| Composition | Results |
|---|---|
| 6F-DI-CY/XU-218 Polyimide | |
| 50/50 mixture | Phase separation |
| 75/25 mixture | Compatible |
| 6F-DI-CY/IP-600 Polyimide | |
| 50/50 mixture | Compatible |
| 75/25 mixture | Compatible |

EXAMPLE IV

The resin of Example I is used to prepare prepregs as follows: 5.5 g of the resin is dissolved in 4.5 g of methyl ethyl ketone solvent. A woven quartz fabric conventionally used to make prepregs is coated with the resin solution by an impregnation treater and then partially cured to form a prepreg.

The prepreg of above is used to prepare a printed circuit board by combining several sheets of prepreg with copper and molding the composite under sufficient heat and pressure to produce a copper clad laminate which is ready for circuitization.

While specific components of the present system are defined above, many other variables may be introduced which may in any way affect, enhance or otherwise improve the system of the present invention. These are intended to be included herein.

Although variations are shown in the present application, many modifications and ramifications will occur to those skilled in the art upon a reading of the present disclosure. These, too, are intended to be included herein.

What is claimed is:

1. A compound of the formula

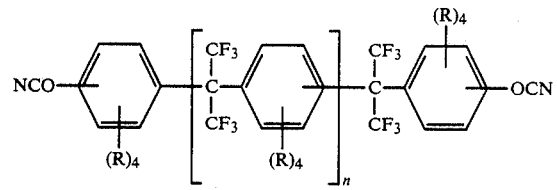

wherein each R group is independently selected from hydrogen, alkyl with 1 to about 8 carbon atoms, alkenyl with 2 to about 8 carbon atoms, aryl or alkaryl with 6 to about 12 carbon atoms, and halogen, and n is an integer from 0 to about 4.

2. The compound of claim 1 wherein all of the R groups are hydrogen.

3. The compound of claim 1 wherein n is an integer selected from 0 and 1.

4. The compound of claim 1 wherein all of the R groups are hydrogen and n is 0.

5. The compound of claim 1 wherein all of the R groups are hydrogen and n is 1.

* * * * *

Disclaimer 4,745,215.—*Robert J. Cox*, Watsonville, Calif.; *William J. Summa*, Endwell; *David W. Wang*, Vestal, both of N. Y. FLUORINE CONTAINING DICYANATE RESINS. Patent dated May 17, 1988. Disclaimer filed Apr. 16, 1990, by the assignee, International Business Machines Corp.

Hereby enters this disclaimer to claims 1, 2, 3, and 4 of said patent.
[ *Official Gazette July 10, 1990* ]